United States Patent [19]
DeWitt et al.

[11] Patent Number: 6,097,881
[45] Date of Patent: Aug. 1, 2000

[54] ELECTRICALLY HEATED CHEMICAL DELIVERY SYSTEM AND METHOD OF MANUFACTURING SAME

[75] Inventors: Donald E. DeWitt, Syracuse; Robert G. Cox, Goshen; Phillip McCoy, Albion, all of Ind.

[73] Assignee: Dekko Heating Technologies, Inc., North Webster, Ind.

[21] Appl. No.: 09/126,472

[22] Filed: Jul. 30, 1998

[51] Int. Cl.[7] .............................. F24F 6/00; H01R 12/00; H01H 85/02
[52] U.S. Cl. .......................... 392/392; 392/387; 439/80; 337/197
[58] Field of Search .................................. 392/386, 387, 392/390, 391, 392; 439/78, 80, 81, 621, 622, 660; 337/197, 198, 199, 186, 187; 252/506, 512, 513, 514; 29/592.1, 610.1, 621

[56] References Cited

U.S. PATENT DOCUMENTS

| | | | |
|---|---|---|---|
| 3,872,280 | 3/1975 | Van Dalen | 219/271 |
| 4,286,251 | 8/1981 | Howell | 252/514 |
| 4,323,293 | 4/1982 | DeRouen et al. | 439/80 |
| 4,425,302 | 1/1984 | Pons Pons | 422/125 |
| 4,549,250 | 10/1985 | Spector | 362/96 |
| 4,734,560 | 3/1988 | Bowen | 219/271 |
| 4,804,821 | 2/1989 | Glucksman | 392/390 |
| 5,111,477 | 5/1992 | Muderlak | 392/390 |
| 5,378,533 | 1/1995 | Ota | 252/512 |
| 5,556,192 | 9/1996 | Wang | 362/276 |
| 5,647,053 | 7/1997 | Schroeder et al. | 392/390 |
| 5,796,914 | 8/1998 | Gatzenmeyer et al. | 392/390 |

FOREIGN PATENT DOCUMENTS 0 334 785 A2  9/1989  European Pat. Off. .......... A61L 9/03

Primary Examiner—Sang Paik
Attorney, Agent, or Firm—Taylor & Aust, P.C.

[57] ABSTRACT

An electrically heated chemical delivery system which is connectable with an electrical receptacle includes a housing with at least one opening therein. A heat actuated chemical pouch is disposed within the housing adjacent to at least one of the openings. A printed circuit board is disposed within and carried by the housing. The board carries a plurality of electrical components thereon, including at least one heater and a light. The board has at least two electrical contacts connected with the electrical components and positioned on an edge thereof. A base is attached with the housing. At least two electrical conductors are carried by the base. Each electrical conductor includes a first terminal end extending from an exterior of the base and a second terminal end engaged with a respective one of the electrical contacts. The first terminal ends are connectable with the electrical receptacle.

24 Claims, 3 Drawing Sheets

ELECTRICALLY HEATED CHEMICAL DELIVERY SYSTEM AND METHOD OF MANUFACTURING SAME

BACKGROUND OF THE INVENTION

1. Field of the Invention

The present invention relates to an electrically heated chemical delivery system, and, more particularly, to an electrically heated chemical delivery system which plugs into an electrical receptacle and delivers an aromatic chemical to an ambient environment.

2. Description of the Related Art

An electrically heated chemical delivery system which is connectable with an electrical receptacle is known. For example, it is known to provide a housing which directly carries a pair of terminals which extend therefrom and may be plugged into a conventional 115 volt electrical receptacle. Electrical terminals are overmolded directly within the housing, and are hard wired using insulated wire and solder connections with an electrical heater disposed within the body. A heat actuated chemical pouch disposed within the body releases an aromatic gas into the ambient environment. Such a chemical delivery system is manufactured by the assignee of the present invention, and sold by S.C. Johnson & Son, Inc., Racine, Wis.

Although an electrically heated chemical delivery system of the type described above was a step forward in the art, a need still exists for a chemical delivery system which is easier to assemble and may be selectively configured to provide more or fewer features to a user.

SUMMARY OF THE INVENTION

The present invention provides a modular electrically heated chemical delivery system with a common housing which may be selectively connected with one of a plurality of differently configured bases and electrical conductors, and which may selectively carry one of a plurality of differently configured printed circuit boards therein.

The invention comprises, in one form thereof, an electrically heated chemical delivery system which is connectable with an electrical receptacle. A housing has at least one opening therein. A heat actuated chemical pouch is disposed within the housing adjacent to at least one of the openings. A printed circuit board is disposed within and carried by the housing. The board carries a plurality of electrical components thereon, including at least one heater and a light. The board has at least two electrical contacts connected with the electrical components and positioned on an edge thereof. A base is attached with the housing. At least two electrical conductors are carried by the base. Each electrical conductor includes a first terminal end extending from an exterior of the base and a second terminal end engaged with a respective one of the electrical contacts. The first terminal ends are connectable with the electrical receptacle.

An advantage of the present invention is that a single housing can be used with multiple base and terminal configurations.

Another advantage is that the plurality of differently configured bases allow the chemical delivery system to be used with different format electrical receptacles which may be used in different countries.

Yet another advantage is that the terminals within the base engage respective electrical contacts on an edge of the printed circuit board concurrently with the base being connected with the housing.

A further advantage is that the housing includes a hole which may be selectively covered or uncovered with a base to allow ambient light to impinge or not impinge on an optional photo-sensitive switch which may be on the printed circuit board.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
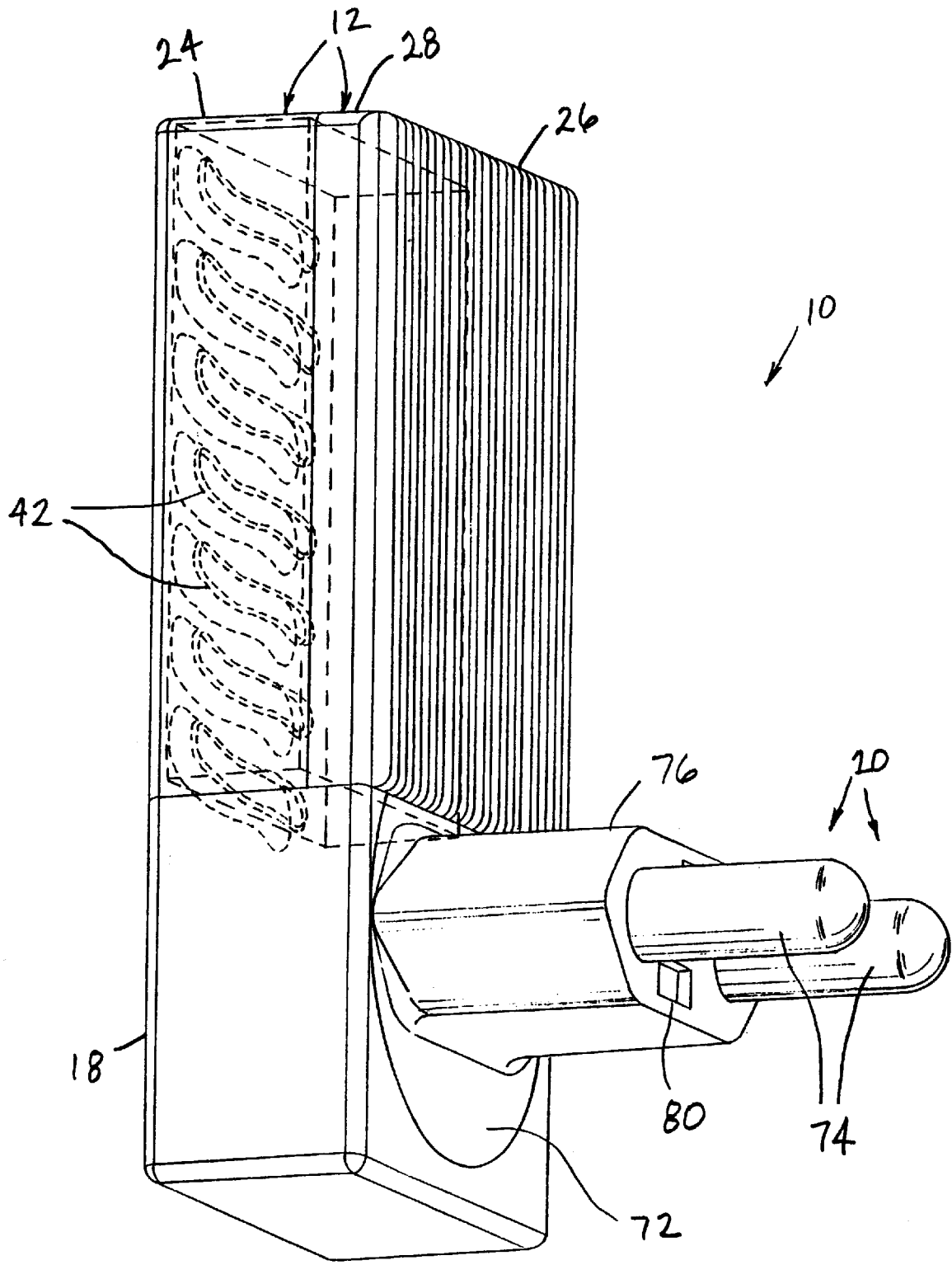
FIG. 1 is a perspective view of an embodiment of an electrically heated chemical delivery system of the present invention.
Figure 2:
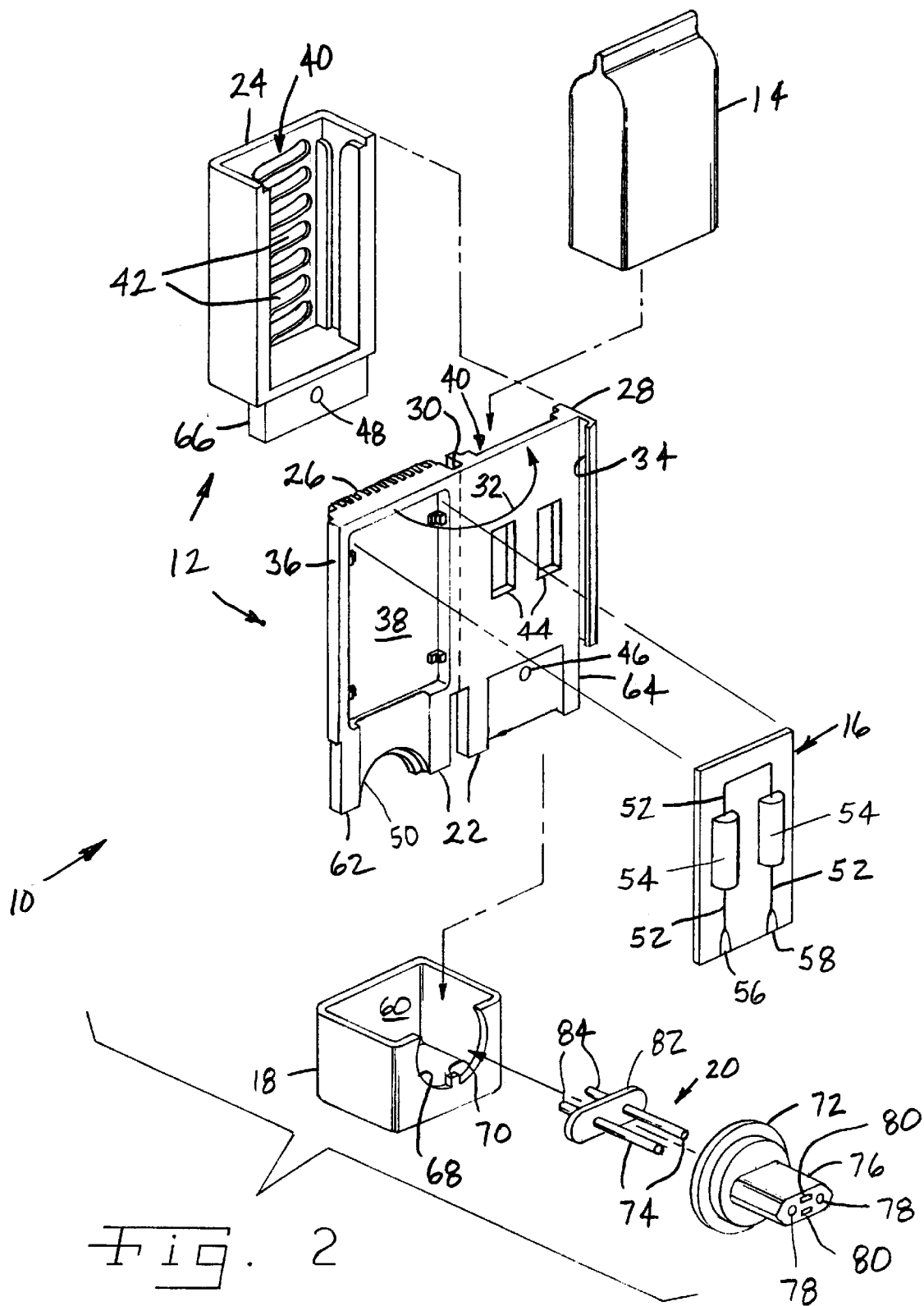
FIG. 2 is an exploded view of the electrically heated chemical delivery system of FIG. 1.

Referring now to the drawings, and more particularly to FIGS. 1 and 2, there is shown an embodiment of an electrically heated chemical delivery system 10 of the present invention which may be connected with an electrical receptacle (not shown). Chemical delivery system 10 generally includes a housing 12, a heat actuated chemical pouch 14, a printed circuit board 16, a base 18 and a pair of electrical conductors 20.

Housing 12 includes a two part body 22 and a face plate 24. Body 22 includes a first part 26 and a second part 28 which are hingedly attached together using a living hinge 30 defined by a thin section of material. First part 26 and second part 28 fold relative to each other, as indicated by arrow 32, and snap lock together using a suitable interlocking snap lock arrangement 34 and 36. First part 26 and second part 28 define a cavity 38 therebetween when snap locked together.

Face plate 24 snap locks with second part 28 of two part body 22. Face plate 24 and second part 28 define a chamber 40 therebetween, into which chemical pouch 14 may be placed during use. A plurality of openings 42 allow the aromatic chemical which is released from chemical pouch 14 to travel into the ambient environment adjacent chemical delivery system 10. Chamber 40 between face plate 24 and second part 28 is also disposed in thermal communication with cavity 38 by a plurality of cut-outs 44 formed in second part 28.

Second part 28 and face plate 24 also each include aligned holes 46 and 48, respectively, which allow ambient light to pass through housing 12 to a photo-sensitive switch (such as a photocell or photo-diode) which may optionally be incorporated into printed circuit board 16. A semi-circular notch 50 in second part 28 allows chemical delivery system 10 to accommodate one of a plurality of different electrical plugs, as will be described in more detail hereinafter. Each differently configured electrical plug allows chemical delivery system 10 to be utilized with a correspondingly configured electrical outlet in a particular country. For example, semi-circular notch 50 and a selected electrical plug mating therewith allow chemical delivery system 10 to be used with differently configured electrical receptacles which may exist, e.g., in the United States, Europe or Korea.

Chemical pouch 14 has a porosity which is sufficient to hold a liquid or gel chemical therein, while at the same time allowing an aromatic gas which is produced upon exposure of pouch 14 to heat to disperse into the ambient environment. Chemical pouch 14 may be of conventional design, and thus will not be described in further detail. An example of such a chemical pouch is sold by S. C. Johnson & Son, Inc., Racine, Wis.

Printed circuit board 16 includes one or more layers of solder runs 52 thereon which allow interconnection between the plurality of electrical components carried thereby. The plurality of electrical components include a pair of heater elements in the form of metal oxide resistors 54. Other electrical components, such as resistors, capacitors, etc., may be included among the plurality of electrical components as necessary, and are not shown for clarity of illustration. The solder runs 52 and electrical components are connected with a pair of electrical contacts 56 and 58 positioned on an edge of printed circuit board 16.

Base 18 includes an inner compartment 60 which is sized to receive lower portions 62, 64 and 66 of each of first part 26, second part 28 and face plate 24, respectively, therein. When coupled with two part body 22 and face plate 24, base 18 includes external dimensions which substantially align with and are substantially flush with the external dimensions of the upper portions (not numbered) of first part 26, second part 28 and face plate 24. Since, in the embodiment shown, printed circuit board 16 does not include a photo-sensitive switch thereon, base 18 likewise does not include a hole which aligns with holes 46 and 48 in second part 28 and face place 24. Thus, base 18 merely covers hole 48 in face plate 24.

Base 18 also includes a semi-circular notch 68 which is complementary and aligned with notch 50 in second part 28. A keying projection 70 extends from the internal periphery of notch 68, and mates with a corresponding keying recess (not shown) in an electrical plug 72.

Electrical plug 72 is configured to mate with a correspondingly configured electrical receptacle with which chemical delivery system 10 is mated. In the embodiment shown, electrical plug 72 includes two first terminals 20 in the form of cylindrical pins 74 which extend from projection 76.

First terminals 20 which extend through apertures 78 in projection 76 are snap locked into place during assembly by engaging transverse surfaces formed within openings 80 with interconnecting disc 82. Second terminals 84 on a side of disc 82 opposite from first terminals 20 are connected with contact pads 56 and 58 of printed circuit board 16, respectively. For example, second terminals 84 may be connected with contact pads 56 via solder connections using insulated electrical wire (not shown).

Figure 3:
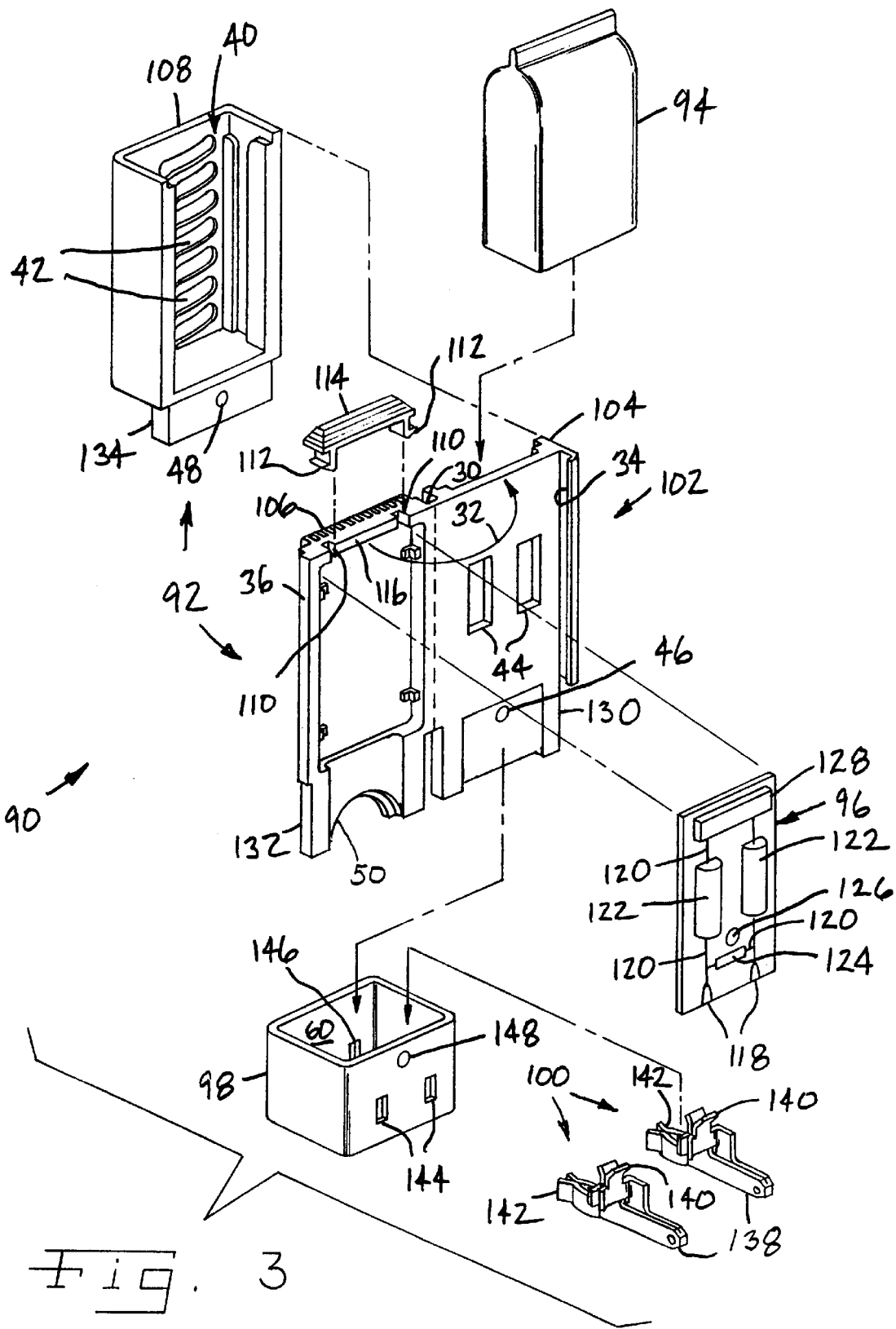
FIG. 3 is an exploded view of another embodiment of an electrically heated chemical delivery system of the present invention.

Referring now to FIG. 3, there is shown another embodiment of an electrically heated chemical delivery system 90 of the present invention. Chemical delivery system 90 generally includes a housing 92, a chemical pouch 94, a printed circuit board 96, a base 98 and a pair of electrical conductors 100.

Housing 92, including two part body 102 with a first part 104 and a second part 106, and a face plate 108 are substantially the same as two part body 22 and face plate 24 shown in the embodiment of FIGS. 1 and 2, and thus will not be described in full detail. Housing 92 differs slightly from housing 12 in that housing 92 includes a pair of cutouts 110 in the top of second part 106 which mate with projections 112 extending from a translucent cover 114. An intermediate portion 116 extending between cutouts 110 is slightly recessed to allow light emitting from cavity 38 to project onto and through translucent cover 114. Translucent cover 114 may be formed, e.g., from a polycarbonate material.

Printed circuit board 96 includes electrical components which are the same as electrical components of printed circuit board 16. For example, printed circuit board 96 includes electrical contacts 118, solder runs 120 and electrical heaters in the form of metal oxide resistors 122. However, printed circuit board 96 also includes other electrical components in the form of an electrical cut-off device 124, a photo-sensitive switch 126 and a light 128.

Electrical cut-off device 124 provides the dual functionality of protecting metal oxide heaters 122 from an over-temperature condition, and also protecting chemical delivery system 90 from an over-current condition associated with an electrical device which may be plugged into chemical delivery system 90. For example, an over-temperature condition may occur if chemical delivery system 90 is plugged into a receptacle operating at a voltage which is higher than the voltage for which metal oxide heaters 122 are designed. An over-current condition may occur if an electrical device requiring a high amperage rating or having an electrical short is plugged into chemical delivery system 90. Depending upon the specific application, electrical cut-off device 124 may be configured to be responsive to either an over-temperature condition or an over-current condition, or both. To provide this dual functionality, electrical cut-off device 124 may be in the form of a relatively fast acting thermal cut-off (TCO) or one or more slow blow fuses, or a combination thereof.

Photo-sensitive switch 126 is positioned on printed circuit board 96 to be adjacent to aligned holes 46 and 48 when printed circuit board 96 is installed within cavity 38. Photo-sensitive switch 126 may be, e.g., configured in the form of a photocell or a photodiode. When the ambient light passing through holes 48 and 46 is below a threshold value, light 128 is energized to cause emission of light through recess 116 and translucent cover 114.

Base 98 includes internal dimensions which are configured to receive lower portions 130, 132 and 134 of first part 104, second part 106 and face plate 108 therein. Base 98 also includes a hole 148 which, when assembled with housing 92, allows ambient light to pass through each of holes 148, 48 and 46 to photo-sensitive sensor 126 located on printed circuit board 96. Base 98 does not include a semi-circular cutout as shown with reference to base 18 in FIGS. 1 and 2. Rather, base 98 directly carries a pair of electrical conductors 136 defining a plug-through arrangement. To hold electrical conductors 136 in place within base 98, suitable supporting structure is molded or otherwise fastened to the inside, bottom of base 98 which engages and supports each of electrical conductors 136. Each electrical conductor 136 includes a first, male terminal end 138, a second, female terminal end 140 and a third, female terminal end 142. Male terminal end 138 extends through the corresponding opening 144 in base 98, and female terminal end 142 is associated with a corresponding electrical socket opening 146 on a side wall of base 98 which is opposite from openings 144. The second, female terminal ends 140 define a socket which extends substantially transverse to the longitudinal direction of each of male terminal end 138 and female terminal end 142, and engages a corresponding electrical contact pad 118 of printed circuit board 96. In the embodiment shown, each electrical conductor 136 is formed from a stamped and bent metal piece which is electrically conductive and relatively resilient. Female terminal ends 140 engage electrical contact pads 118 of printed circuit board 96 with a compressive force to ensure proper electrical contact, and female terminal ends 142 engage blades of a conventional 115 volts male plug-in to allow use of chemical delivery system 90 without reducing the number of plug-ins which are available at the electrical receptacle in a wall.

To assemble chemical delivery system 90, printed circuit board 96 is placed within two part body 102 such that photo-sensitive sensor 126 is adjacent to hole 46. Projections 112 of translucent cover 114 are aligned with cutouts 110 in second part 106, and first part 104 is then folded around living hinge 30 such that first part 104 and second part 106 snap lock together. When locked together, printed circuit board 96 and translucent cover 114 are held in place relative to two part body 102. Face plate 108 is then snap locked onto first part 104, thereby defining a chamber 40 therebetween receiving a chemical pouch 94 therein. Electrical conductors 136 are positioned within base 98 such that male terminal ends 138 extend from openings 144, and female terminal ends 142 are positioned adjacent to and in association with socket openings 146. Base 98 is then slid over the lower portions 130, 132 and 134 of first part 104, second part 106 and face plate 108, respectively. When base 98 is engaged with two part body 102 and face plate 108, second, female terminal ends 140 of electrical conductors 136 respectively engage electrical contact pads 118 of printed circuit board 96 in a slightly clamping manner, thereby ensuring good electrical contact. Concurrently with the seating of base 98 and engagement between second terminals 140 and electrical contact pads 118, hole 148 in base 98 also aligns with holes 46 and 48 to allow ambient light to pass through to photo-sensitive switch 126.

During use, male terminal ends 142 are plugged into a female plug-in of a standard 115 volt electrical receptacle, common in the U.S. Power applied to male terminal ends 138 is sourced to electrical components on printed circuit board 96 through female terminal ends 140 and electrical contacts 118. Heat generated from metal oxide resistors 122 is transferred through cutouts 44 to the heat actuated chemical pouch 94 within chamber 40. The chemical pouch allows an aromatic gas to flow through openings 42 in face plate 108 to the ambient environment. If an absence of light is sensed through holes 148, 48 and 46 using photo-sensitive switch 126, then light 128 is actuated to emit light through translucent cover 114. A user that desires to utilize the electrical plug-in in the electrical receptacle to which chemical delivery system 90 is coupled may plug the male prongs of a conventional electrical plug into socket openings 146 of base 98, thereby engaging the blades with female terminal ends 142.

In the embodiment shown, holes 148, 48 and 46 are aligned with each other to allow ambient light to travel therethrough to impinge upon photo-sensitive switch 126. However, it will also be appreciated that a different type of sensor other than a light sensor may be aligned with holes 148, 48 and 46. For example, a motion detector or infrared sensor may be used to detect the presence of a person in the proximity of chemical delivery system 90. The sensor then may be used to alter the amount of electrical power which is applied to metal oxide heaters 122 and/or light 128. In this manner, anazmia to the aromatic gas (i.e., an acquired insensitivity to the aroma which is built up over time) is avoided.

Moreover, rather than providing some type of sensor which is aligned with holes 148, 48 and 46, it is also possible to provide an indicator such as a light emitting diode (LED) or an audible alarm which is aligned with holes 148, 48 and 46 to alert a user of an operating condition associated with chemical delivery system 90. For example, an LED aligned with holes 148, 48 and 46 may be actuated to indicate to a user that chemical pouch 14 is approaching an end of its useful life and should be replaced. The useful life of chemical pouch 14 may be determined dependent upon a length of time which metal oxide resistors 54 have been actuated since chemical pouch 14 was first placed in use. When a new chemical pouch 14 is placed within chamber 40, a manual reset switch, or a two-position lever within chamber 40, indicating that an old chemical pouch 14 was removed and a new chemical pouch 14 was inserted, may be used to start a new time period associated with the estimated life of the new chemical pouch.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An electrically heated chemical delivery system which is connectable with an electrical receptacle, comprising:
   a housing having at least one opening;
   a heat actuated chemical pouch disposed within said housing adjacent to at least one said opening;
   a board disposed within and carried by said housing, said board carrying a plurality of electrical components thereon, including at least one heater and a light, said board having at least two electrical contacts connected with said electrical components and positioned on at least one edge thereof;
   a base attached and nonmonolithic with said housing; and
   at least two electrical conductors carried by said base, each said electrical conductor including a first terminal end extending from an exterior of said base and a second terminal end engaged with a respective one of said electrical contacts, said first terminal ends being connectable with the electrical receptacle.

2. The electrically heated chemical delivery system of claim 1, wherein said at least two electrical contacts comprise two electrical pads positioned on an edge thereof.

3. The electrically heated chemical delivery system of claim 1, wherein said board is a printed circuit board.

4. The electrically heated chemical delivery system of claim 1, wherein said housing includes a face plate, and wherein said at least one opening comprises a plurality of openings in said face plate.

5. The electrically heated chemical delivery system of claim 1, wherein said heat actuated chemical pouch comprises a heat actuated aromatic, chemical pouch.

6. The electrically heated chemical delivery system of claim 1, wherein said first terminal ends correspond to standard configuration terminals adapted for plugging into a corresponding conventional electrical receptacle.

7. The electrically heated chemical delivery system of claim 1, wherein said base includes at least two electrical socket openings and wherein at least two of said electrical conductors include a third terminal end, each said third terminal end associated with a respective said electrical socket opening.

8. The electrically heated chemical delivery system of claim 7, wherein each said first terminal end is a male terminal end and each said third terminal end is a female terminal end.

9. The electrically heated chemical delivery system of claim 8, wherein each said second terminal end is a female terminal end.

10. The electrically heated chemical delivery system of claim 7, wherein said first terminal end and said third terminal end of each said conductor are associated with generally opposite sides of said base, and wherein each said second terminal end is interposed between said first terminal end and said second terminal end of said corresponding electrical conductor.

11. The electrically heated chemical delivery system of claim 1, wherein said plurality of electrical components carried by said board further include at least one electrical cut-off device, each said electrical cut-off device being responsive to one of an over-temperature condition and an over-current condition.

12. The electrically heated chemical delivery system of claim 11, wherein said at least one electrical cut-off device defines a dual means for:

protecting said at least one heater from an over-temperature condition; and protecting said electrically heated chemical delivery system from an over-current condition.

13. The electrically heated chemical delivery system of claim 1, wherein said at least one heater comprises a plurality of metal oxide heaters.

14. The electrically heated chemical delivery system of claim 1, wherein said plurality of electrical components carried by said board further include a photo-sensitive switch, and wherein said housing includes a hole adjacent to said switch which extends to an ambient environment.

15. The electrically heated chemical delivery system of claim 14, wherein said photo-sensitive switch comprises a photo cell.

16. A method of manufacturing an electrically heated chemical delivery system which is connectable with an electrical receptacle, comprising:

providing a housing having at least one opening;

placing a heat actuated chemical pouch within said housing adjacent to at least one said opening;

positioning a board within said housing, said board carrying a plurality of electrical components thereon, including at least one heater and a light, said board having at least two electrical contacts connected with said electrical components and positioned on at least one edge thereof;

installing at least two electrical conductors within a base chosen from a plurality of bases, each of said plurality of bases being differently configured relative to each other and attachable with said housing, each said electrical conductor including a first terminal end and a second terminal end, each said first terminal end extending from an exterior of said chosen base and connectable with the electrical receptacle; and attaching said chosen base with said housing, whereby each said second terminal end is engaged with a respective one of said electrical contacts.

17. The method of claim 16, wherein said chosen base includes at least two electrical socket openings and wherein at least two of said electrical conductors include a third terminal end, each said third terminal end associated with a respective said electrical socket opening.

18. The method of claim 17, wherein each said first terminal end is a male terminal end and each said third terminal end is a female terminal end.

19. The method of claim 18, wherein each said second terminal end is a female terminal end.

20. The method of claim 17, wherein said first terminal end and said third terminal end of each said conductor are associated with generally opposite sides of said chosen base, and wherein each said second terminal end is interposed between said first terminal end and said second terminal end of said corresponding electrical conductor.

21. The method of claim 20, wherein said board is a printed circuit board, and wherein said at least two electrical contacts comprise two electrical pads positioned on an edge thereof.

22. An electrically heated chemical delivery system which is connectable with an electrical receptacle and receives a heat actuated chemical pouch therein, said electrically heated chemical delivery system comprising:

a housing configured to receive the heat actuated chemical pouch therein and having at least one opening;

a heat actuated chemical pouch disposed within said housing adjacent to at least one said opening;

a board disposed within and carried by said housing, said board carrying a plurality of electrical components thereon, including at least one heater, said board having at least two electrical contacts connected with said electrical components and positioned on at least one edge thereof;

a base attached with said housing; and at least two electrical conductors carried by said base, each said electrical conductor including a first terminal end extending from an exterior of said base and a second terminal end engaged with a respective one of said electrical contacts, said first terminal ends being connectable with the electrical receptacle.

23. The electrically heated chemical delivery system of claim 1, wherein said base is detachable from said housing.

24. The electrically heated chemical delivery system of claim 1, wherein each said second terminal end is a female terminal end, each said female terminal end defining a means for detachably engaging said respective one of said electrical contacts.

* * * * *